US012685828B2

(12) United States Patent
Odelberg et al.

(10) Patent No.: US 12,685,828 B2
(45) Date of Patent: Jul. 21, 2026

(54) BULK HANDLING FEATURE

(71) Applicant: SHL MEDICAL AG, Zug (CH)

(72) Inventors: Linda Odelberg, Ekerö (SE); Erika André, Saltsjö-Boo (SE); Pär Leander, Nacka (SE); Anders Holmqvist, Värmdö (SE)

(73) Assignee: SHL Medical AG, Zug (CH)

( * ) Notice: Subject to any disclaimer, the term of this patent is extended or adjusted under 35 U.S.C. 154(b) by 1258 days.

(21) Appl. No.: 17/418,381

(22) PCT Filed: Dec. 12, 2019

(86) PCT No.: PCT/EP2019/084858
§ 371 (c)(1),
(2) Date: Jun. 25, 2021

(87) PCT Pub. No.: WO2020/143989
PCT Pub. Date: Jul. 16, 2020

(65) Prior Publication Data
US 2022/0062562 A1     Mar. 3, 2022

(30) Foreign Application Priority Data
Jan. 9, 2019     (EP) ..................................... 19150988

(51) Int. Cl.
*A61M 5/20*     (2006.01)
*A61M 5/32*     (2006.01)
(52) U.S. Cl.
CPC ....... *A61M 5/3243* (2013.01); *A61M 2207/00* (2013.01)
(58) Field of Classification Search
CPC ........... B23P 13/00; B23P 13/02; B23P 17/00;
B23P 25/00; B29B 11/08; B29L 2031/7544; B29L 2031/753; A61M 2207/00; A61M 5/31511; A61M 5/3243; A61M 2005/2006; A61M 5/20; B29C 2791/001; B29C 2793/0054; B29C 2949/072; B29C 2949/0715; B29C 49/071; B29C 49/20;
(Continued)

(56) References Cited

U.S. PATENT DOCUMENTS 10,159,800 B2     12/2018 Sall
2013/0253435 A1     9/2013 Vernizeau et al.
(Continued)

FOREIGN PATENT DOCUMENTS

EP          3326671 A1     5/2018
WO     WO-2010136076 A1 *  12/2010     .......... A61M 5/2033
(Continued)

OTHER PUBLICATIONS

International Search Report and Written Opinion for Int. App. No. PCT/EP2019/084858, mailed Mar. 3, 2020.
(Continued)

*Primary Examiner* — Laura A Bouchelle
*Assistant Examiner* — Sarah Dympna Grasmeder
(74) *Attorney, Agent, or Firm* — McDonnell Boehnen Hulbert & Berghoff LLP

(57) ABSTRACT
A support element for a component that has at least two elongated members directed generally in a common direction and having free ends, wherein the support element is arranged to connect and support the at least two elongated members.

16 Claims, 4 Drawing Sheets

(58) Field of Classification Search
CPC .. B29C 66/5221; B65D 1/0238; B65D 47/36;
B65B 3/022; Y10T 156/1062
See application file for complete search history.

(56) References Cited

U.S. PATENT DOCUMENTS

| | | | |
|---|---|---|---|
| 2013/0331796 | A1 | 12/2013 | Wozencroft |
| 2014/0148763 | A1 | 5/2014 | Karlsson et al. |
| 2016/0287798 | A1 | 10/2016 | Holmqvist |
| 2017/0304599 | A1* | 10/2017 | Dombrowski ....... B65D 1/0238 |
| 2018/0008779 | A1 | 1/2018 | Hautaviita et al. |
| 2020/0385181 | A1* | 12/2020 | Hiemer .................. B65D 47/36 |

FOREIGN PATENT DOCUMENTS

| | | | | |
|---|---|---|---|---|
| WO | WO-2011007626 | A1 * | 1/2011 | ............ G09B 19/10 |
| WO | 2017/144211 | A1 | 8/2017 | |

OTHER PUBLICATIONS

Examination Report issued by the European Patent Office in application No. 19 816 760.3 dated Dec. 23, 2024.

\* cited by examiner

BULK HANDLING FEATURE

CROSS REFERENCE TO RELATED APPLICATIONS

The present application is a U.S. National Phase Application pursuant to 35 U.S.C. § 371 of International Application No. PCT/EP2019/084858 filed Dec. 12, 2021, which claims priority to European Patent Application No. 19150988.4 filed Jan. 9, 2019. The entire disclosure contents of these applications are herewith incorporated by reference into the present application.

TECHNICAL AREA

The present application relates to bulk handling of components for assembly into devices such as medicament delivery devices.

BACKGROUND

Many components that are used in devices such as medicament delivery devices have special forms and shapes for performing different functions. One such general shape that is rather common for elongated injectors such as pen injectors and auto-injectors is an elongated shape that often is used in order to fit in the elongated housings of the medicament delivery devices.

One such type of elongated component often also entails two elongated members that are positioned on each side of a central structure. As shown in FIG. 1, this could for example be a needle shield 10 that protrudes out of a proximal end of a housing 12 of a medicament delivery device, where the needle shield also is designed as a trigger mechanism in that when the device is pressed against an injection site, the needle shield is moved in the distal direction and will affect for instance a drive unit 14 that will perform a penetration or an injection. The needle shield then often has two elongated arms 16 that are extending on opposite sides of a medicament container 18 or a medicament container holder 20 that is placed centrally in the housing.

Another type of component may be a plunger rod holder 22 of a drive unit 14 as shown in FIG. 2, having two distally directed arms that are designed to surround and support a plunger rod 24.

The design of these types of components makes handling of the components in bulk very difficult since they have a tendency to get tangled into each other with the elongated members. This is a major drawback if they are to be used in high volume assembly where automatic feeders, sorters and the like component handling equipment is used. Apart from the tangling aspect, the components may also be deformed by the weight of other components when handled in bulk.

So even though these designs are good and sometimes necessary in a functional aspect of the components, they are not good in a bulk handling aspect. Thus, there is room for improvements regarding the bulk handling aspects of this type of components.

SUMMARY

In the present disclosure, when the term "distal" is used, this refers to the direction pointing away from the dose delivery site. When the term "distal part/end" is used, this refers to the part/end of the delivery device, or the parts/ends of the members thereof, which under use of the medicament delivery device is/are located furthest away from the dose delivery site. Correspondingly, when the term "proximal" is used, this refers to the direction pointing to the dose delivery site. When the term "proximal part/end" is used, this refers to the part/end of the delivery device, or the parts/ends of the members thereof, which under use of the medicament delivery device is/are located closest to the dose delivery site.

The object of the present application is to remedy the drawbacks of the state of the art. This object is solved by a support element according to the independent patent claims. Preferable embodiments of the application form the subject of the dependent patent claims.

According to a main aspect of the application, a support element is provided for a component that comprises at least two elongated members directed generally in a common direction and having free ends, wherein said support element is arranged to connect and support the at least two elongated members. With this solution, the risk of entanglement of the elongated members of several components is greatly reduced or minimized. Further the risk of damage of the elongated members due to weight of a large number of other components stacked in bulk is also greatly reduced or minimized.

According to a preferable solution, the support elements may be arranged adjacent the free ends of the at least two elongated members.

The support element may be integrated with the elongated members when the component is manufactured, and in particular may be molded in one piece with the component. The support element may further be provided with detachment areas adjacent the elongated members, wherein the detachment areas may be arranged with lesser material than the rest of the support element.

A method according to the present application may comprise the step of detaching the support element from a component prior to assembly of said component. In this regard, the step of detaching the support element may comprise any of blade cutting sawing or melting.

These and other aspects of, and advantages with, the present disclosure will become apparent from the following detailed description of the disclosure and from the accompanying drawings.

BRIEF DESCRIPTION OF DRAWINGS

In the following detailed description of the disclosure, reference will be made to the accompanying drawings, of which

DETAILED DESCRIPTION

Figure 1:
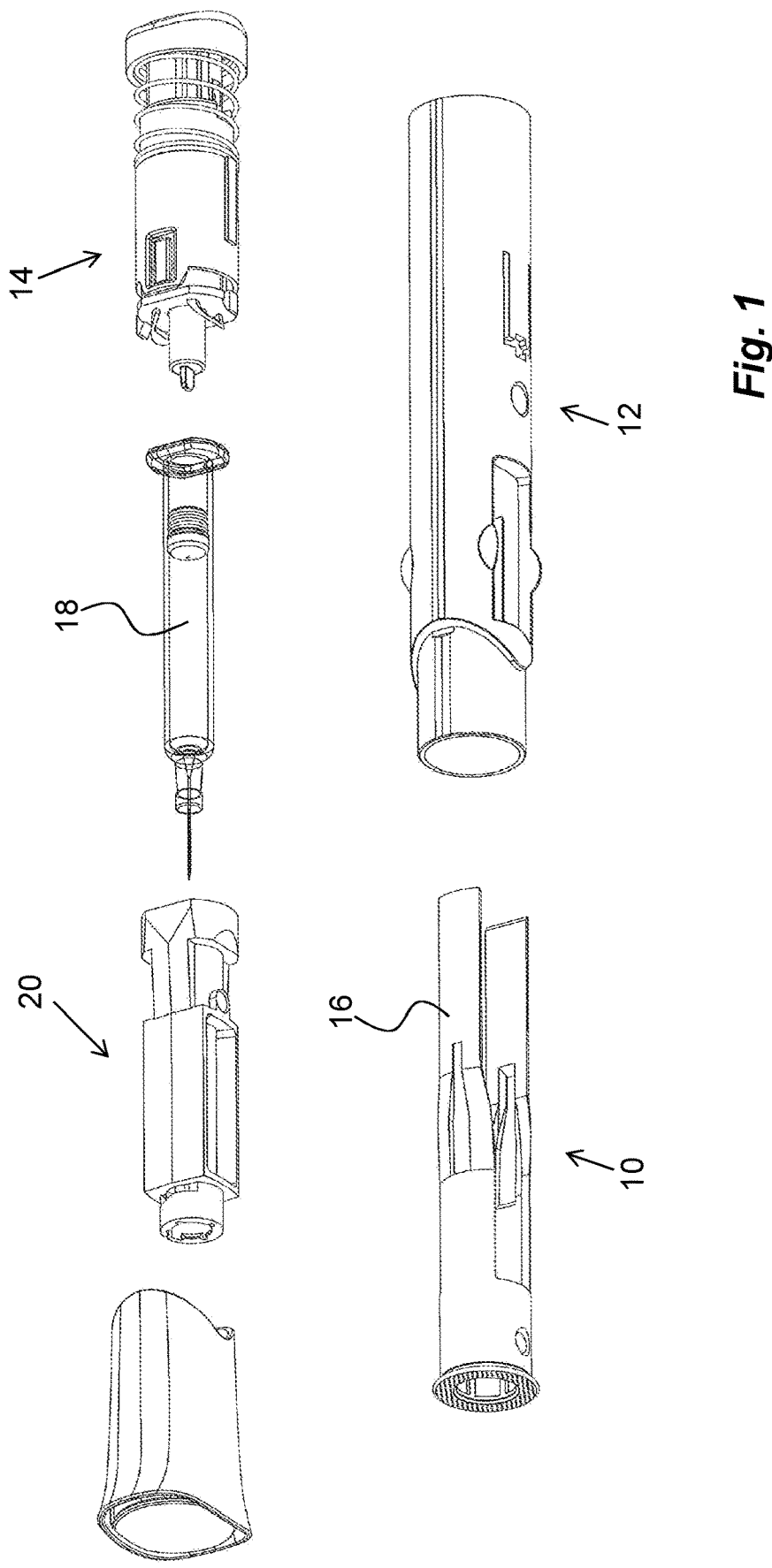
FIGS. 1 and 2 show state of the art medicament delivery devices provided with components that are difficult to handle in bulk.
Figure 2:
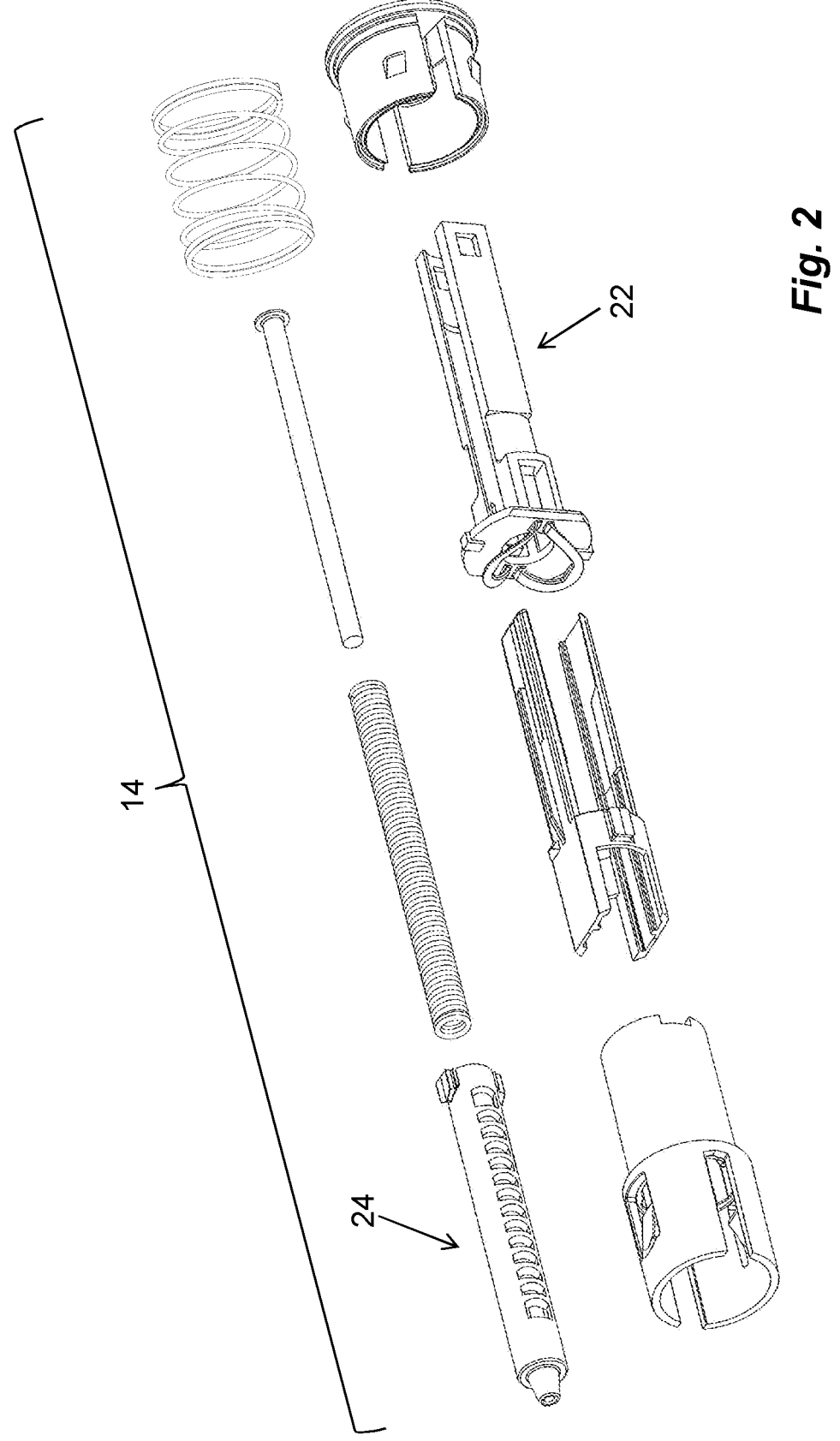
Figures 3, 4:
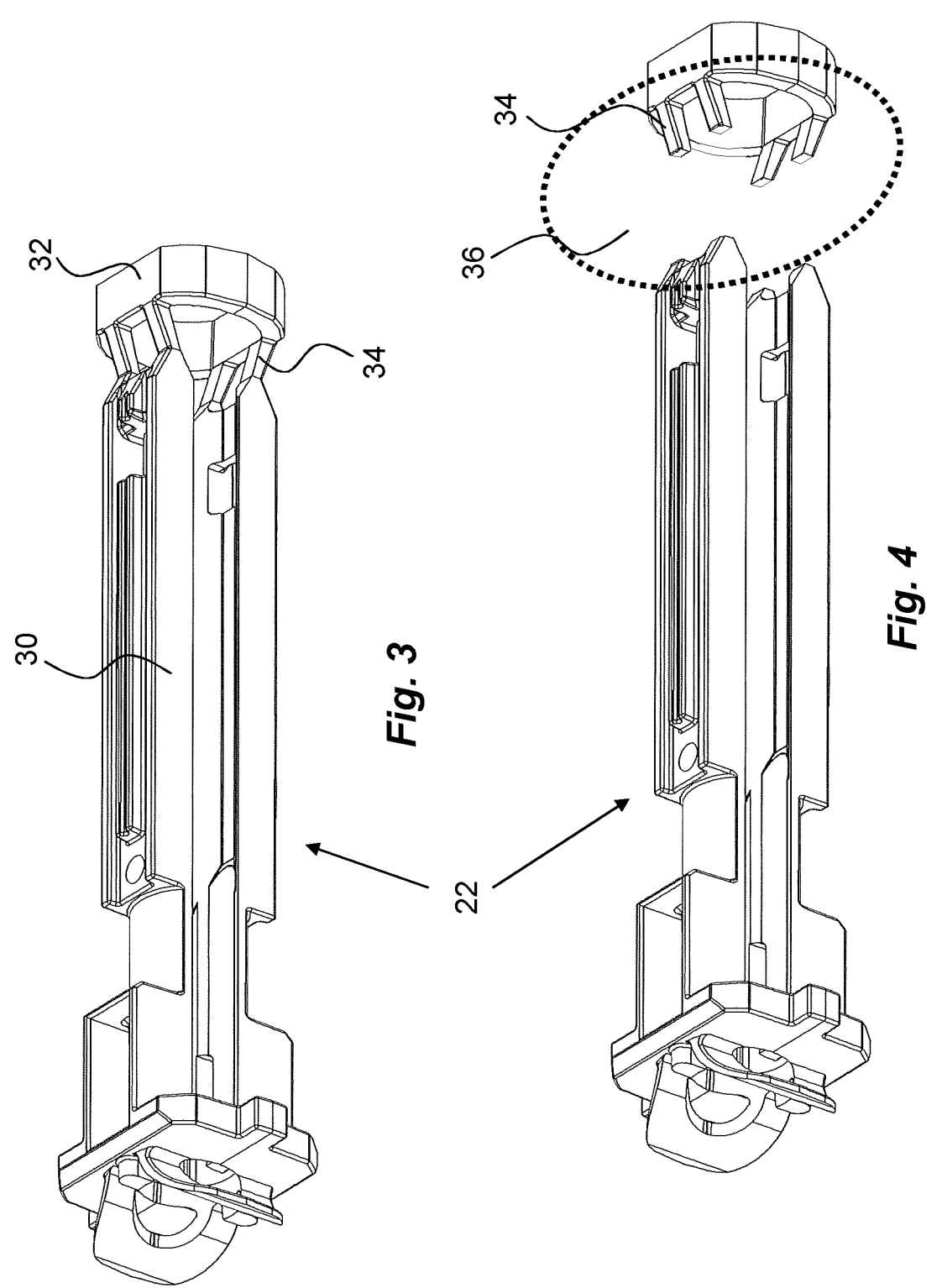
FIG. 3 shows a component comprised in a power unit of a medicament delivery device arranged with a support element to improve bulk handling.
FIG. 4 shows the component with the support element detached.

FIG. 3 shows one example of a component that is difficult to handle in bulk. In the shown example, the component is a plunger rod holder 22 that is used in a power pack 14 of a medicament delivery device. The plunger rod holder 22 is arranged with two arms 30 extending in a distal direction, wherein the arms are designed to run on opposite sides of a plunger rod 24.

When the component 22 is molded, a connecting support element 32 is integrated with the free ends of the arms 30. This will prevent the arms 30 from entangling in other components when placed together in bulk. As seen in FIGS. 3 and 4, the support element 32 is provided with thinner areas 34 adjacent the ends of the arms 30. When the components 22 have been sorted by an appropriate machine and are ready for assembly, the support element 32 will be detached from the arms 30, as seen in FIG. 4. This may be done by different techniques and equipment 36 such as blade cutting, sawing, or heating by laser for instance. The thinner areas 34 will then facilitate the detaching operation. It is however to be understood that this is not necessary to have thinner areas for the detachment.

Figure 5:
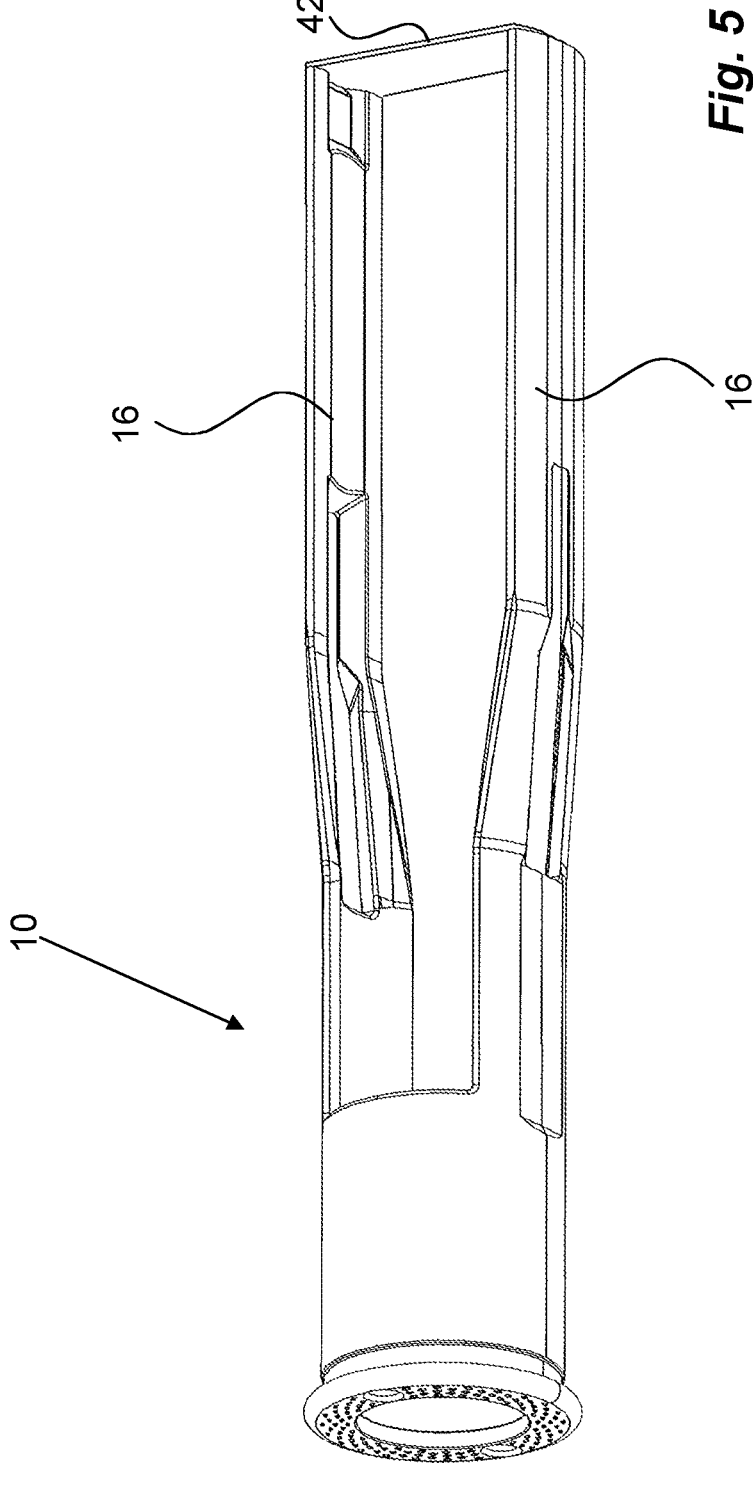
FIG. 5 shows a needle shield of a medicament delivery device also arranged with a support element to improve bulk handling.

For instance, FIG. 5 shows another component that is problematic to handle in bulk. In this case, a needle shield 10 is provided having two elongated arms 16. The free ends of the arms 16 are arranged with a connecting support element 42 that in the embodiment shown has a plate-shape. Here no thinned areas are arranged. Instead, an appropriate cut is made at the distal end of the arms 16, detaching the support element 42 from the component 10.

With the above, it is apparent that the support elements may have a number of different designs in order to provide the desired support for the components to be handled in bulk.

It is to be understood that the embodiments described above and shown in the drawings are only to be regarded as non-limiting examples, and that the present application may be modified in many ways within the scope of the patent claims.

The invention claimed is:

1. A component of a medical delivery device comprising:
at least two elongated members directed generally in a common direction and having free ends; and
a support element configured to connect and support the at least two elongated members from being entangled, wherein the support element is detachable prior to final assembly of the medical delivery device.

2. The component of the medical delivery device according to claim 1, wherein the support element is arranged adjacent the free ends of the at least two elongated members.

3. The component of the medical delivery device according to claim 1, wherein the support element is integrated with the elongated members when the component is manufactured.

4. The component of the medical delivery device according to claim 3, wherein the support element is molded in one piece with the component.

5. The component of the medical delivery device according to claim 1, wherein the support element further comprises:
detachment areas adjacent the elongated members.

6. The component of the medical delivery device according to claim 5, wherein the detachment areas are arranged with lesser structural material than the rest of the support element.

7. A method of manufacturing a component of a medical delivery device comprising: fabricating the component according to claim 1; and removing the support element prior to final assembly of the medical delivery device.

8. A process of assembling a medical delivery device comprising: providing the component of the medical delivery device according to claim 1; detaching from the component the support element prior to final assembly of the medical delivery device; and removing the detached support element from the process of assembling the medical delivery device.

9. The process according to claim 8, wherein the step of detaching the support element comprises cutting, snapping, breaking, sawing, melting, bending, twisting of a detachment area that connects the support element to the component.

10. A component of a medical delivery device configured to surround and support a plunger rod of the medical delivery device, the component comprising:
at least two elongated members directed generally in a common direction and having free ends; and
a support element configured to connect and support the at least two elongated members of the component, wherein the support element is detachable prior to final assembly of the medical delivery device.

11. The component according to claim 10, wherein the support element is further configured to prevent the at least two elongated members of the component from being entangled when placed together in bulk.

12. The component according to claim 11, wherein the support element is arranged adjacent the free ends of the at least two elongated members.

13. The component according to claim 11, wherein the support element is integrated with the elongated members when the component is manufactured.

14. The component according to claim 13, wherein the support element is molded in one piece with the component.

15. The component according to claim 11, further provided with detachment areas adjacent the elongated members.

16. The component according to claim 15, wherein the detachment areas are arranged with lesser structural material than the rest of the support element.

* * * * *